United States Patent [19]

Bard

[11] Patent Number: 5,580,523
[45] Date of Patent: Dec. 3, 1996

[54] INTEGRATED CHEMICAL SYNTHESIZERS

[76] Inventor: Allen J. Bard, 6202 Mountain Climb Dr., Austin, Tex. 78731

[21] Appl. No.: 221,931

[22] Filed: Apr. 1, 1994

[51] Int. Cl.$^6$ .............................. G01N 30/02; B01J 19/00
[52] U.S. Cl. ..................... 422/50; 422/70; 422/81; 422/82.01; 422/82.05; 422/99; 422/110; 422/116; 422/119; 422/129; 422/134; 210/198.2; 435/287.1; 435/288.6; 435/288.7
[58] Field of Search ........................... 422/50, 68.1, 70, 422/81, 82.01, 82.05, 99, 108, 110, 116, 119, 129, 131, 134; 210/198.2; 73/61.1 C; 435/287.1, 288.6, 288.7

[56] References Cited

U.S. PATENT DOCUMENTS

| | | |
|---|---|---|
| 2,761,882 | 9/1956 | Hulse et al. . |
| 3,531,258 | 9/1970 | Merrifield et al. . |
| 3,557,077 | 1/1971 | Brunfeldt et al. . |
| 3,647,390 | 3/1972 | Kubodera et al. . |
| 3,951,741 | 4/1976 | Pfaender et al. ................. 195/29 |
| 4,276,048 | 6/1981 | Leaback . |
| 4,362,699 | 12/1982 | Verlander et al. ................ 422/131 |
| 4,458,066 | 7/1984 | Caruthers et al. ................ 536/27 |
| 4,483,964 | 11/1984 | Urdea et al. .................. 524/54.11 |
| 4,701,304 | 10/1987 | Horn et al. .................... 422/62 |
| 4,704,256 | 11/1987 | Hood et al. .................... 422/68 |
| 4,728,502 | 3/1988 | Hamill ....................... 422/116 |
| 4,748,002 | 5/1988 | Neimark et al. ................. 422/116 |
| 4,800,166 | 1/1989 | Horn et al. .................... 436/55 |
| 4,816,513 | 3/1989 | Bridgham et al. ............... 525/54.11 |
| 4,861,866 | 8/1989 | Durrum et al. .................. 530/333 |
| 4,960,566 | 10/1990 | Mochida et al. ................. 422/65 |
| 4,961,915 | 10/1990 | Martin ....................... 422/116 |
| 5,037,882 | 8/1991 | Steel ........................ 525/54.11 |
| 5,089,232 | 2/1992 | May ......................... 422/83 |
| 5,110,431 | 5/1992 | Moring ....................... 204/180.1 |
| 5,132,012 | 7/1992 | Miura et al. ................... 210/198.2 |
| 5,175,209 | 12/1992 | Beattle et al. ................. 525/54.11 |
| 5,176,881 | 1/1993 | Sepaniak et al. ................ 422/82 |
| 5,194,133 | 3/1993 | Clark et al. ................... 204/299 R |
| 5,250,263 | 10/1993 | Manz ........................ 422/81 |
| 5,252,294 | 10/1993 | Kroy et al. .................... 422/102 |
| 5,296,375 | 3/1994 | Kricka et al. .................. 435/291 |
| 5,304,487 | 4/1994 | Wilding et al. ................. 435/291 |

OTHER PUBLICATIONS

"Molecular Manufacturing for the Environment" K. Eric Drexier Institute for Molecular Manufacturing, Los Altos, CA, 94022 pp. 263–265.
"Process Miniaturisation—A Route to Total Environmental Acceptability?" R. S. Benson (Fellow) * and J. W. Ponton (Fellow) ** ICI Engineering Department of Chemical Engineering, University of Edinburgh pp. 160–168.
D. Jed Harrison et al., *Micromachining a Miniatured Capillary Electrophoresis–Based Chemical Analysis System on a Chip*, Science, vol. 261, Aug. 13, 1993, pp. 895–897.
Research News, *The Small Wonders of Microengineering*, vol. 253, Jul. 26, 1991, pp. 387–388.
ISCO, Inc., Catalog 27, Jun. 1991, pp. 1, 86, 89, 72–73.
SGE Catalog, pp. 32, 86, 117–119.
Alltech Associates Catalog, pp. 559–564, 567, 569, 571.

*Primary Examiner*—David A. Redding
*Attorney, Agent, or Firm*—John W. Ryan; Michael S. Marcus

[57] ABSTRACT

A modular reactor system and method for synthesizing chemical compounds characterized by a uniform temperature throughout the reaction mixture by use of a continuous flow reactor under high pressure. The apparatus includes a number of generic components such as pumps, flow channels, manifolds, flow restrictors, and valves. Modular reactors, separator and analyzers on an assembly board provide a system where a modular reactor unit has an I.D. of up 100 μm to optimize control of residence time within a reaction zone.

11 Claims, 7 Drawing Sheets

FIG. 9

INTEGRATED CHEMICAL SYNTHESIZERS

FIELD OF THE INVENTION

This invention relates to an improved method and apparatus for continuously synthesizing chemical compounds under controlled and regulated reaction conditions. More particularly, this invention relates to a modular multi-component system with interchangeable microreactors, that can be used in tandem, series, or individually. Flow and reaction conditions of the modular multi-component system can be monitored to regulate the reaction process and/or create an optimal environment for the synthesis of the desired chemical compounds.

BACKGROUND OF THE INVENTION

Complex inorganic and organic compounds, e.g., drugs, monomers, organometallic compounds, semiconductors, polymers, peptides, oligonucleotides, polynucleotides, carbohydrates, amino acids, and nucleic acids belong to a class of materials having significant diagnostic, medicinal and commercial importance. Many techniques have been developed to produce these materials. However, the systems necessary to carry-out and prepare or synthesize these complex materials are inefficient, wasteful and often times require reagent quantities far in excess of what is available. This is especially the case in those instances where milliter quantities are involved. The use of conventional substrates requires larger sized systems with the incumbent process control problems. Additionally, reagent or reactant stability must be considered and accurately controlled to render the process efficient in yield and cost.

The production of these complex materials requires a versatile system that can handle different reaction and separatory schemes. Most synthesizers provide only for a single type of reactor, e.g., electrochemical, catalytic, solid phase support, enzymatic, photochemical, or hollow chamber.

For example, U.S. Pat. No. 4,517,338 to Urdea teaches a system for sequencing amino acids that uses one or more elongated tubular reaction zones. The reactors for each reaction zone are similar in structure with an internal diameter (I.D.) of a 0.1 to 1.0 cm. Each of the reactors needs a glass frit to support the solid-phase material.

U.S. Pat. No. 4,960,566 to Mochida relates to an automatic analyzer for conveying reagent coated capillary tubes along process lines where reagents are added, reacted and analyzed. The Mochida patent indicates at Column 3 that the inner diameter of the capillary tubes appears to be no smaller than 0.95 mm. The process of Mochida provides for serial processing of reaction tubes of a common design. Independent temperature control of parallel tubes and modularity are not provided.

U.S. Pat. No. 4,276,048 to Leaback teaches capillary size reaction containers for volumetric transfer of fluids to a microtitre tray. The system is essentially batch-like and does not involve continuous flow or automatic valving to selectively direct the flow of a particular reagent to one reaction column as opposed to another to provide for amino acid sequencing within the tube.

U.S. Pat. No. 5,176,881 to Sepaniak et al. teaches a fiber optic-based regenerable biosensor that uses a capillary feed mechanism.

U.S. Pat. No. 4,362,699 to Verlander et al. relates to high pressure peptide synthesizers and uses a plurality of reservoirs that communicate via a switching valve to a reactor 90.

The Verlander system was designed to overcome the limitations of the Merrifield system which apparently had a limitation of synthesizing peptides having no more than 10 amino acids. The system can also include a mixer upstream of the reactor to mix the protected amino acid solution and the appropriate activating reagent. Column 6 lines 3–12. The system is automated and the reactor column contains a polystyrene resin which is derivatized with a protected amino acid.

U.S. Pat. No. 4,458,066 to Caruthers et al. teaches an amino acid synthesizer and uses a plurality of reagent reservoirs connected via a manifold to a tubular reactor. The reactor column 10 includes a solid silica gel matrix derivatized for the sequencing operation and, via a valve can be communicated to a UV detector 58. The reactor is taught to be sized for a 1 ml. volume.

U.S. Pat. No. 4,728,502 Hamill relates to an amino acid sequencer that utilizes a plurality of stacked disks each having a plurality of chambers and resulting in a plurality of parallel columns. Although the contents of each chamber of each disk are removable, the respective columns formed by a series of chambers in the stacked disk are not.

U.S. Pat. No. 4,961,915 to Martin relates to a DNA sequencing system. A rotatable turntable conveys fluids along narrow channels that are open on an upper end. This allows individual dispensing of additional reagents along the length of the channel. The Martin patent does not provide a continuous flow valved reaction system or direct in-line valving to control reagents directly to one or more channels. In addition, the grooves or channels are in a common base and replacement or scale up is not possible.

The object of the subject invention is to provide an Integrated Chemical Synthesizer (ICS) system that is modular in design and provides for continuous flow operation. The modular nature of the ICS system allows for the use of one or more of the same type of reactor, or a variety of different types of reactors, each having microliter capacity. The reactors of the ICS system are capable of being used individually, together, and interchangeably with one another and can be of the thermal, electrochemical, catalytic, enzymatic, photochemical, or hollow chamber type. The modular nature of the system, component parts, e.g., the reactors, flow channels, sensors, detectors, temperature control units, allows easy replacement and/or interchangeability of the component parts and provides a versatility not offered by existing systems.

The ICS system provides for uniform temperature control for continuous flow reactors under elevated pressures. This allows for precise control of residence time within a reaction zone. ICS synthesizers would thus exhibit a number of advantages when compared to conventional systems of larger size. Heat transfer, which depends upon the ratio of surface area (A) to volume (V), would be much better for the smaller reactors. This is a major advantage, for example, in capillary zone electrophoresis compared to large scale gel electrophoresis. This configuration also allows faster heat dissipation and faster thermal control.

The ICS system would not only present better control of reaction conditions, but it would allow for quenching reactions at certain stages to prevent further reaction. The ICS system would also, due to its modular nature, provide for serial placement of reactors to allow controlled sequential reactions of intermediates. Moreover, it should be much easier to scale-up reactions based on the ICS approach because one would simply add additional modules of exactly the same type to increase output. For industrial synthesis, the ICS approach would eliminate proceeding from a bench scale reactor through a variety of different pilot plant configurations to a full-sized reactor.

Moreover, the inherent redundancy of multiple parallel ICS reactors implies fewer operational problems with the failure of a few reactors, especially if the system is set up for easy replacement and repair of a single ICS line. As a result, such systems are probably inherently much safer. The rupture of a single ICS reactor, even at high temperature and pressure, would cause negligible damage since the total volume and amounts of reactants released would be small. This would be especially beneficial when carrying out reactions under extreme conditions, e.g., the high temperatures and pressure in supercritical water and other fluids. Overall the ICS system should result in better yields of products with less waste and disposal problems because of better control of reaction variables.

As a result of the ICS modular system, the problems of inefficiency, lack of versatility, down-time, reagent/reactant waste and excessive cost have been overcome.

SUMMARY OF THE INVENTION

Accordingly, the present invention provides a novel system for synthesizing chemical compounds. The system of the present invention can also synthesize compounds under a variety of process conditions, e.g., uniform temperature in a continuous flow reactor under high pressure, non-uniform temperatures and high pressure.

In accordance with one aspect of the present invention a modular multicomponent system is provided. The system, e.g. a kit, provides a reaction system capable of handling a variety of reactions by using a reactor unit having a reaction chamber with an I.D. of from about 1 µm up to about 1 mm, and more preferably 1–100 µm. Specifically, a modular "chip" type reactor unit is formed by applying a photoresist layer onto an upper surface of a $SiO_2$ or Si substrate and forming a reactor design thereon. The reactor design is developed and etched with acid to form a reactor chamber having an ID less than 100 µm. The chamber is covered and the unit mounted on an assembly board containing fluid conveying channels, with fastening means, to provide for flow to and from the reactor chamber.

In accordance with another aspect of the present invention, a modular multicomponent system containing a plurality of interchangeable reaction vessels, alike or different, in parallel or series, and capable of handling reactions volumes from about 1nL up to about 10 µL, and more preferably 1nL–10 µL is provided.

In still another aspect of the present invention, both organic and inorganic compounds can be synthesized.

In yet another aspect of the present invention, a novel system capable of regulating extreme conditions (e.g., supercritical temperatures and pressures) is provided. This system for synthesizing compounds provides a means for avoiding potential explosions and provides a reliable method for heat dissipation.

DETAILED DESCRIPTION OF THE PREFERRED EMBODIMENTS

The present invention is broadly directed toward a total modular system that can use a plurality of replaceable and interchangeable cylindrical or rectangular reactors in combination with a mass-based sensor. Generally, the ICS system can include (1) fluid flow handling and control components; (2) mixers; (3) reaction "chip type" units; (3) separatory devices; (4) process variable detectors and controllers; and (5) a computer interface for communicating with a master control center.

The ICS system may also include a support structure for detachably retaining the various components of the system. The support structure can be of the "assembly board type" that will contain pre-arranged flow channels and connector ports. The desired components of the system can be fastened into these connectors by pins. The flow control components that make-up the ICS system can include pumps, flow channels, manifolds, flow restrictors, valves, etc. These components will have the necessary fittings that allow them to be sealed with the pre-arranged or selectively located flow channels or connectors. The flow system can also include detachable mixing devices, e.g., static or ultrasonic, some of which can be "chip like" in design. The reaction units, whether "chip like" or not, can be of the thermal, electrochemical, photochemical, pressure type and be rectangular or cylindrical in shape.

The separatory components can provide for membrane separation, concurrent or countercurrent flow extraction, chromatographic separation, electrophoretic separation, or distillation. The detectors can include electrochemical, spectroscopic or fluorescence based detectors to monitor the reactants, intermediates, or final products.

The ICS system can include a plurality of individual, detachable reaction units. With a plurality of units, one of the reaction units may be structurally different and capable of permitting a different chemical process of being performed. For example there may be thermal and photochemical units or electrochemical, thermal and pressure units. The ICS system can also include a detachable separation chamber, and an analyzer capable of monitoring and/or controlling a process variable. More specifically, a typical embodiment utilizes flow channels, a flow mixer, at least one electrochemical reaction chamber, an electrophoretic separation chamber, and an electrochemical analyzer.

In accordance with the preferred embodiment of the present invention, an apparatus for achieving the synthesis described above is illustrated in FIG. 1–9.

The basic concept of the subject invention is to produce a modular system, with components (reactors, separation chambers, analyzers, etc.) that are inexpensive and easily assembled. The subject invention can be assembled on a flow channel assembly board in the same way integrated circuitry chips and other electrical components are assembled on a circuit board. In the ICS system various reactors, analyzer(s), e.g., "chip units," are put together on an "assembly board". Two approaches to assembling such systems would be (a) custom design chips and assembly boards or, (b) the current capillary high pressure liquid chromatography (HPLC)-capillary zone electrophoresis (CZE) approach with microbore tubing (silica, stainless steel) and various connectors, injectors, pumps, etc. In case (a) the chips could be made from silica ($SiO_2$)(glass), silicon (Si)(as integrated circuit chips), polymers (plastic), and/or metal (stainless steel, titanium).

An example of fabricating a chip unit 100 according to the invention is shown in FIGS. 1a–1d. With reference to FIGS. 1a–1d, a substrate of $SiO_2$ or Si is designed to include a rectangular reaction chamber 4. The chamber 4 is formed by photolithographic processes such as those currently used for integrated circuits and circuit boards. A photoresist layer 2 is deposited on the upper surface 6 of the $SiO_2$ or Si block substrate 1 and, the desired pattern 3 is formed in layer 2 by exposure to the proper image and development techniques. The rectangular reactor chamber 4 is formed by etching the preformed pattern into the substrate, e.g., with HF for $SiO_2$ to the extent necessary to form a chamber having the desired volume. For complex structures, multiple photolithographic processes may be necessary. Flow channels for the reactor are similarly fabricated using photolithography from the other side of the substrate. A second photoresist layer 7 is placed on lower surface 6, exposed to form port openings 8 and 9. Thereafter, channels 10 and 11 are formed to provide flow communication to reactor chamber 4. Finally, a cover 12 is attached to close the upper surface 5 to form a top of the reactor 4 and produce the finished chip. Photoresist layers 2 and 7 also include a plurality of patterns 13–16 and 17–20 formed thereon so that through channels for fastening pins can be formed. The reactor could also be fabricated at one time, alternatively, with plastic materials, by injection molding or casting techniques. Micromachining (e.g., using the scanning tunneling microscope or scanning electrochemical microscope) of metals and semiconductor substrates could also be used to make the moduclar units of the subject invention.

Table 1 shows volume parameters for various ICS reactors.

| VOLUMES ICS REACTORS | | | | | |
|---|---|---|---|---|---|
| Calculation of ICS Reactor Volumes Cylindrical reactor, $V=\pi d^2 L/4$ | | | Rectangular reactor, $V=d^2 L$ | | |
| d (μm) | L (μm) | V (μL) | d (μm) | L (μm) | V (μL) |
| 1 | 10 | 7.85E–09 | 1 | 10 | 1.00E–08 |
| 1 | 100 | 7.85E–08 | 1 | 100 | 1.00E–07 |
| 1 | 1000 | 7.85E–07 | 1 | 1000 | 1.00E–06 |
| 1 | 1.00E+04 | 7.85E–06 | 1 | 1.00E+04 | 1.00E–05 |
| 10 | 10 | 7.85E–07 | 10 | 10 | 1.00E–06 |
| 10 | 100 | 7.85E–06 | 10 | 100 | 1.00E–05 |
| 10 | 1000 | 7.85E–05 | 10 | 1000 | 1.00E–04 |
| 10 | 1.00E+04 | 7.85E–04 | 10 | 1.00E+04 | 1.00E–03 |
| 100 | 10 | 7.85E–05 | 100 | 10 | 1.00E–04 |
| 100 | 100 | 7.85E–04 | 100 | 100 | 1.00E–3 |
| 100 | 1000 | 7.85E–03 | 100 | 1000 | 1.00E–2 |
| 100 | 1.00E+04 | 7.85E–02 | 100 | 1.00E+04 | 1.00E–1 |
| 1000 | 10 | 7.85E–03 | 1000 | 10 | 1.00E–2 |
| 1000 | 100 | 7.85E–02 | 1000 | 100 | 1.00E–1 |
| 1000 | 1000 | 7.85E–01 | 1000 | 1000 | 1.00E+00 |
| 1000 | 1.00E+04 | 7.85E+00 | 1000 | 1.00E+04 | 1.00E+01 |
| 1 μm=(1e–4)cm | | | 1000 μm=1 mm | | |
| 1 μm^3(1e–9)μL | | | 1E4 μm=1 cm | | |

1 nL=(1e–3)μL
1 pL=(1e–6)μL
1 aL=(1e–9)μL

Figure 1A:
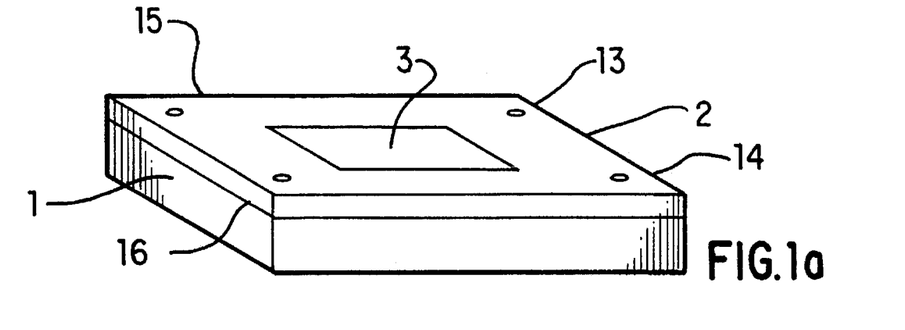
FIGS. 1a–1d show a fabricated chip type reactor unit for the ICS modular system.
Figure 1B:
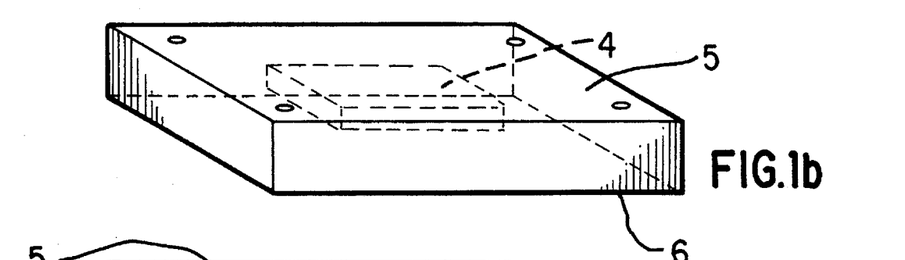
Figure 1C:
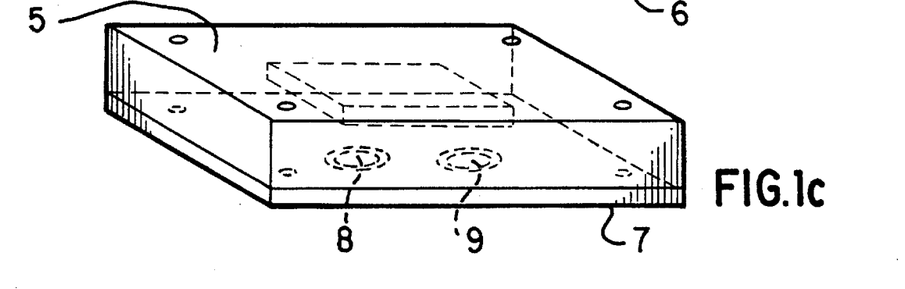
Figure 1D:
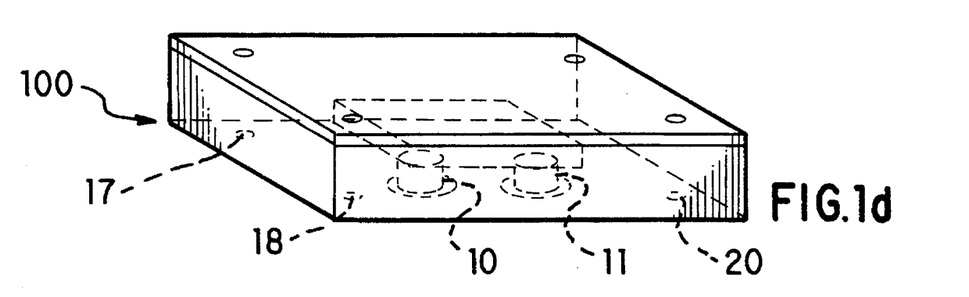
Figure 2:
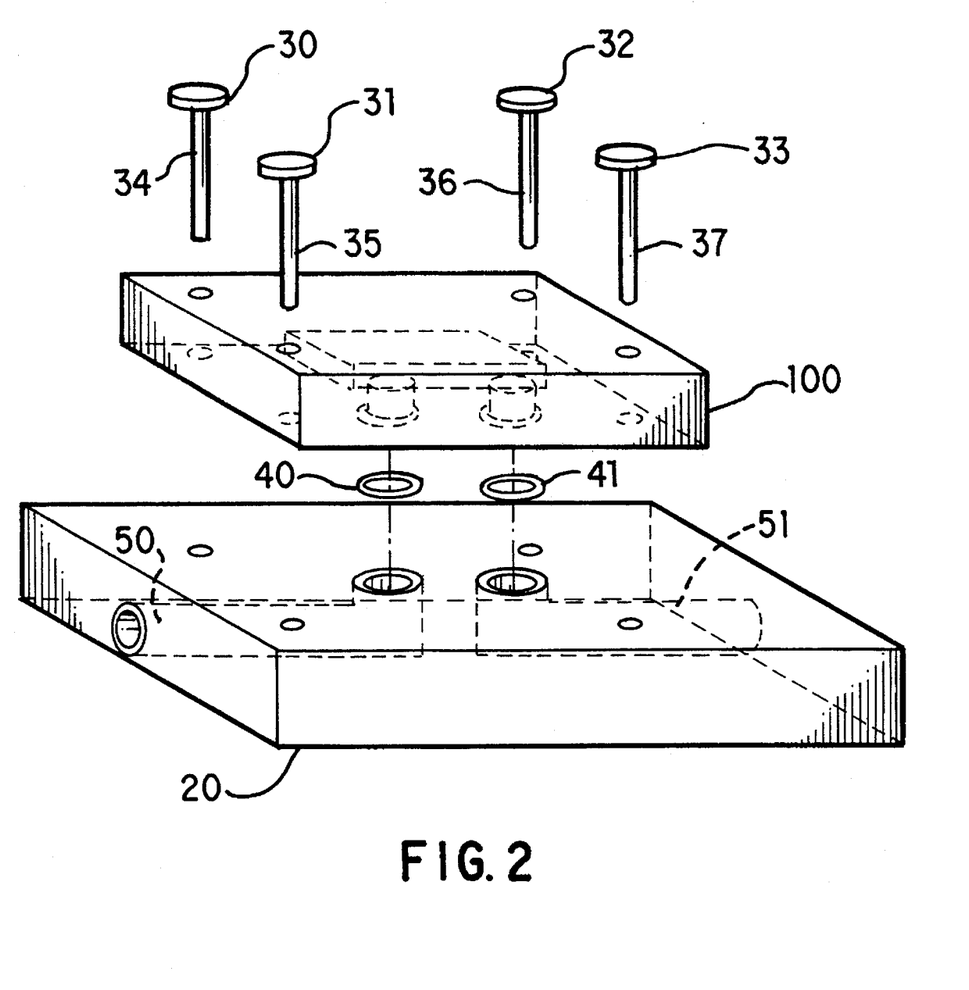
FIGS. 2 illustrates an exploded view of a chip type reactor unit and the fluid delivery flow channels of an assembly board according to the present invention.

The different kinds of chip units produced according to the subject invention could then be connected to the assembly board containing the desired flow connections (FIG. 2) and also (not shown) electrical connections to electrodes, heaters, etc. FIG. 2 uses O-rings 40 and 41 (Teflon, Viton) to connect the chip channels 10 and 11 to the corresponding channels 50 and 51 on assembly board 20 and pins 30–37 (or clips) to hold the chip to board 20.

Figure 3:
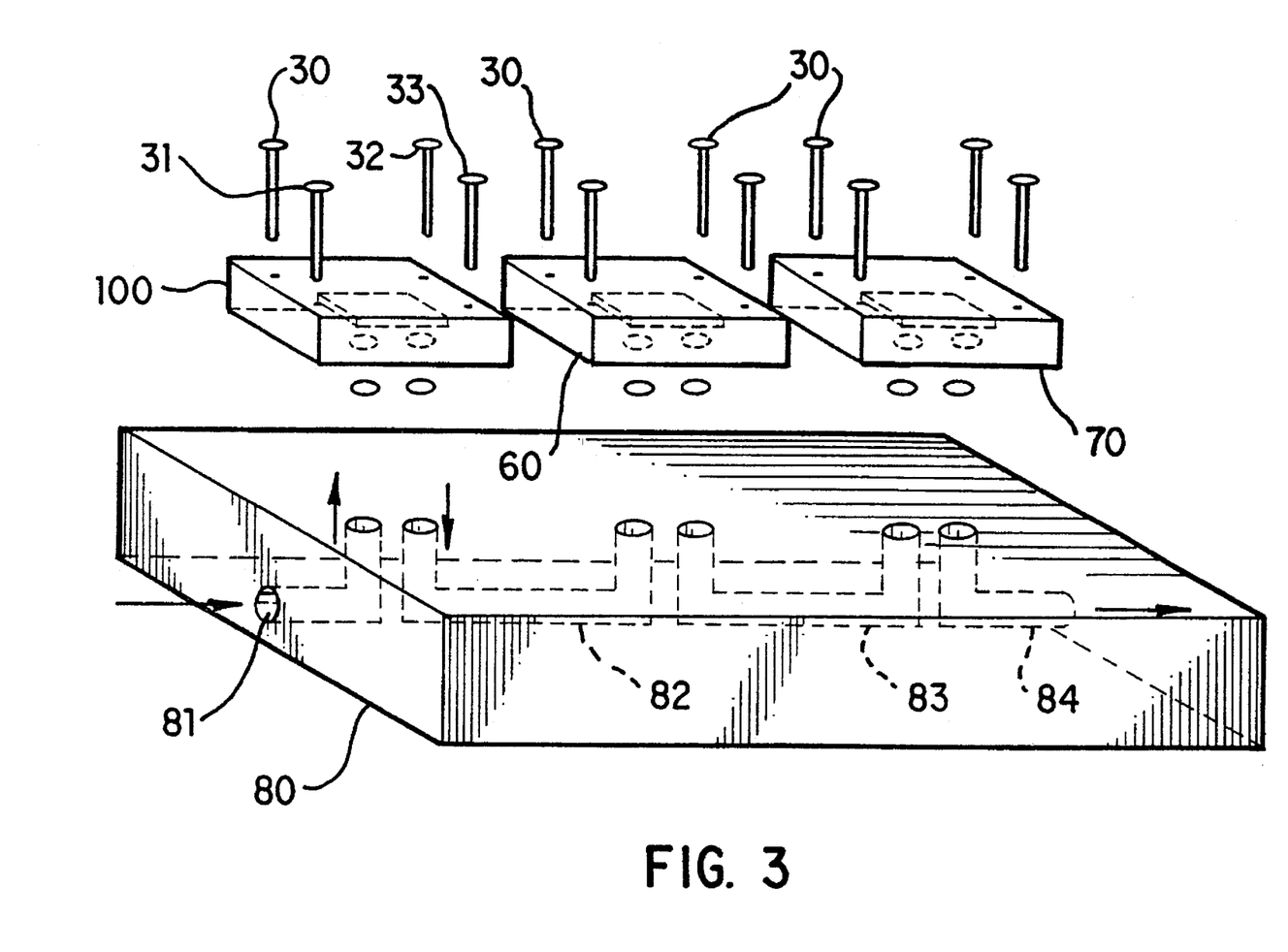
FIG. 3 is an exploded view of one embodiment of the ICS system.

FIG. 3 shows an assembly of several different chips on a single board with interconnections. In FIG. 3 units 100, 60, and 70 are respectively a reactor, a separator and an analyzer. The housings for separator 60 and analyzer 70 are formed in a manner similar to that of reactor unit 100 described above, but include the requisite, structures and components to perform the designated process, e.g., separation, analysis.

In FIG. 3, pins 30–33 connect the units 100, 60 and 70 to assembly board 80 containing channels 81–84 therein. Channels 81 and 82 respectively communicate with channels 10 and 11 in reactor unit 100. Similarly, channels 82 and 83 communicate with the corresponding channels in unit 60 and channels 83 and 84 communicate with the channels in unit 70.

Alternatively capillary tubing for reactors, detectors, etc., following current HPLC-CZE practice, sized in accordance with the subject disclosure may be assembled on a support board in a similar manner (not shown).

For capillary tubing, connectors, pumps, etc., using the capillary HPLC approach can be obtained from manufacturers, such as, Valco, Swagelok, and Waters. Specialized materials useful in the subject invention reactors and separators can be made from Naflon (ion-exchange) hollow fibers and are manufactured by DuPont.

If a glass substrate is used for the "chip" units, the walls are already $SiO_2$. If a Si substrate is used, $SiO_2$ can be formed by oxidation in air under controlled temperature conditions. For metal substrates, e.g., Ti, a protective and insulating film ($TiO_2$) can also be formed by air or anodic oxidation. It is also possible to coat the walls of the tube with catalyst particles, organic films for separations, etc.

Figure 4:
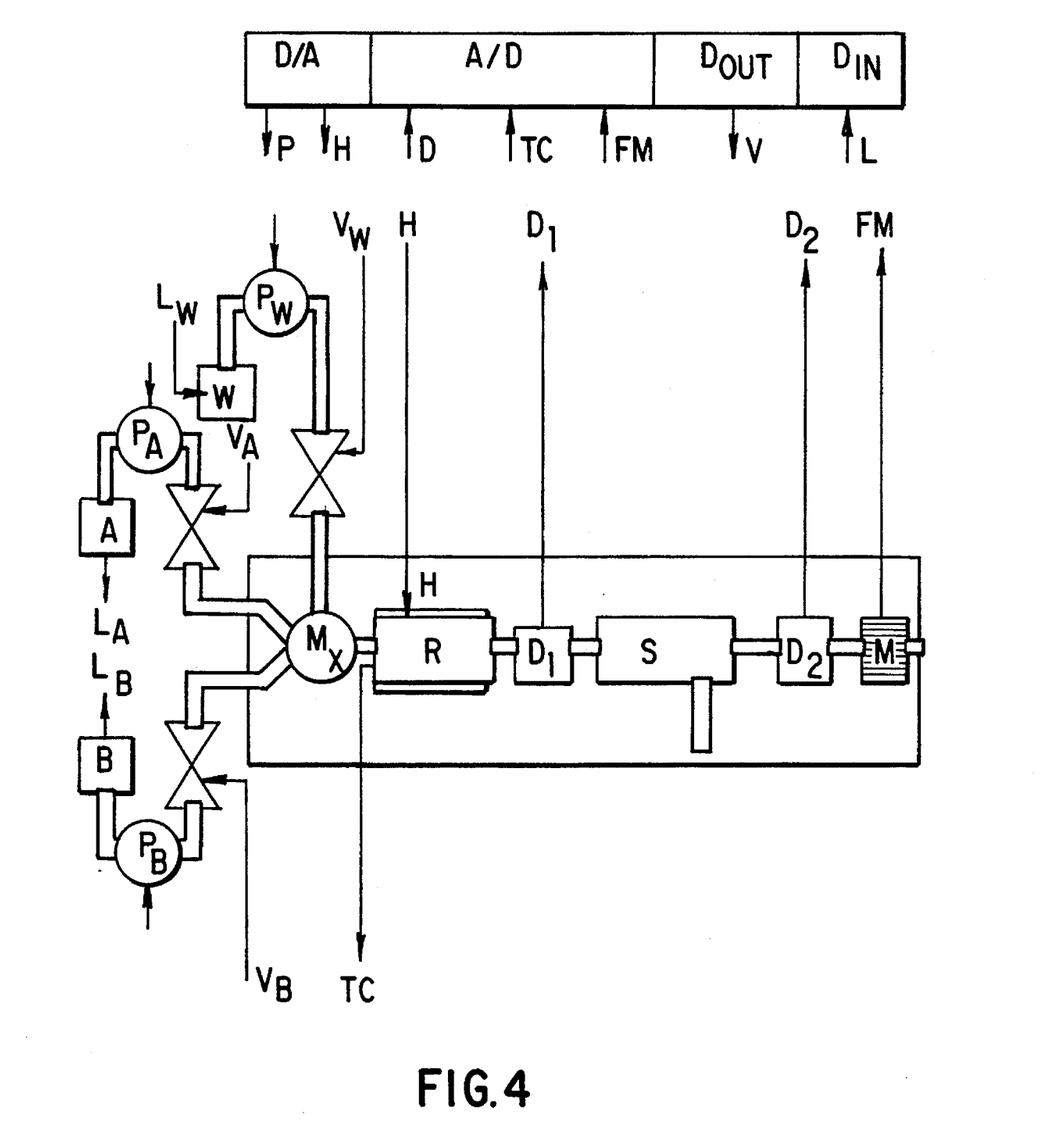
FIG. 4 shows an exemplary ICS system with fluid control and computer interfacing according to the subject invention.

FIG. 4 includes an assembly board schematically showing the "chip" type processing units of the subject invention.

The assembly board includes a reactor R formed in a manner similar to unit 100 above, but includes a heat transfer system. The reactor R communicates with a chip type mixer $M_x$ at the upstream end and a chip type detector $D_1$, e.g., unit 100, at the downstream end. The detector $D_1$ communicates with a chip type separator, e.g., unit 60, which in turn is in fluid communication with a second chip type detector unit $D_2$, e.g., unit 70.

The system of FIG. 4 operates as follows: reagents A and B via pressure actuated pumps $P_A$ and $P_B$, and valves $V_A$ and $V_B$ sequentially or simultaneously flow to the mixer $M_x$. If isolation of a reagent is necessary, after reagent A is fed to mixer $M_x$ and discharged to the reactor $R_1$, a wash fluid W is conveyed via pump $P_W$ and valve $V_W$ to the mixer $M_x$ and discharged. Signals from detectors $D_1$, $D_2$, thermocouple TC, and flowmeter FM are transmitted to the computer through interface 90 to control the flow of reagents A and B and temperature, or any additional reagents according to the process to be performed by the subject invention.

Having now generally described this invention, the following examples are included for purposes of illustration and are not intended as any form of limitation.

EXAMPLE 1

Figure 5:
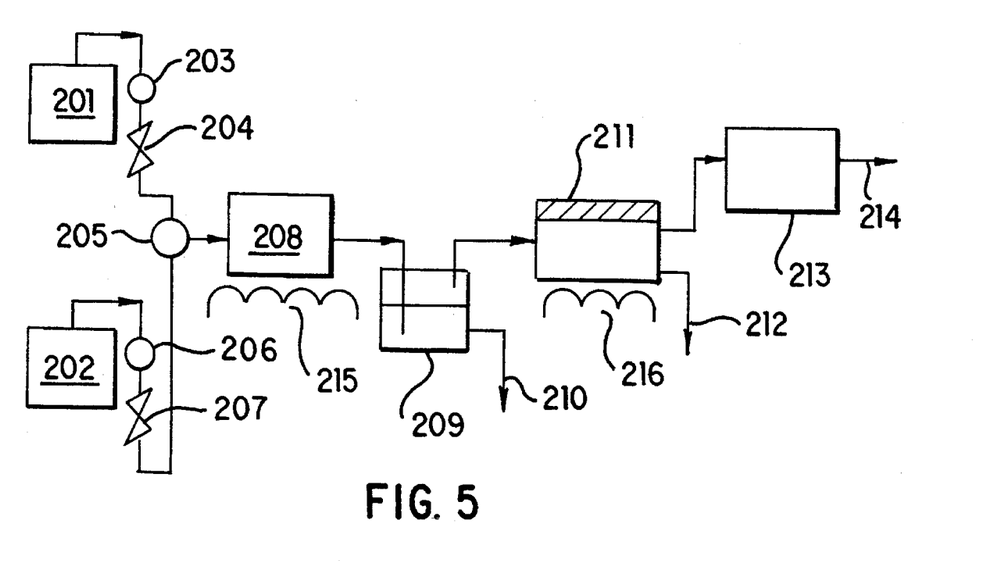
FIG. 5 is a flow chart for preparing t-BuCl using the subject invention.

Thermal Conversion of t-butanol to t-butyl Chloride $(CH_3)_3-C-OH + Cl^- + H^+ \rightarrow (CH_3)_3CCl + H_2O$ With reference to FIG. 5, solutions of concentrated hydrochloric acid 201 and t-butanol 202 are metered through pumps 203, 206 and valves 204, 207 to a mixer 205 to the reaction chamber 208. Temperature in the reaction chamber 208 is controlled via a heating/cooling system 215 on the assembly board, e.g., 80, to maintain the reaction temperature (measured by a thermocouple) at about 30°–40° C. The two phases that form are separated in the separator chamber 209 and further purification of t-BuCl can be accomplished, if desired, by distillation at 50° C. in chamber 213 with product being withdrawn via line 214. HCl and $H_2O$ are withdrawn via line 210 and waste is discharged via line 212.

EXAMPLE 2

Photochemical Conversion of Dibenzylketone $$Ph-CH_2-\overset{\overset{O}{\|}}{C}-CH_2-Ph \xrightarrow{h\nu} CO + Ph-CH_2-CH_2-Ph$$
(DBK)

Figure 6:
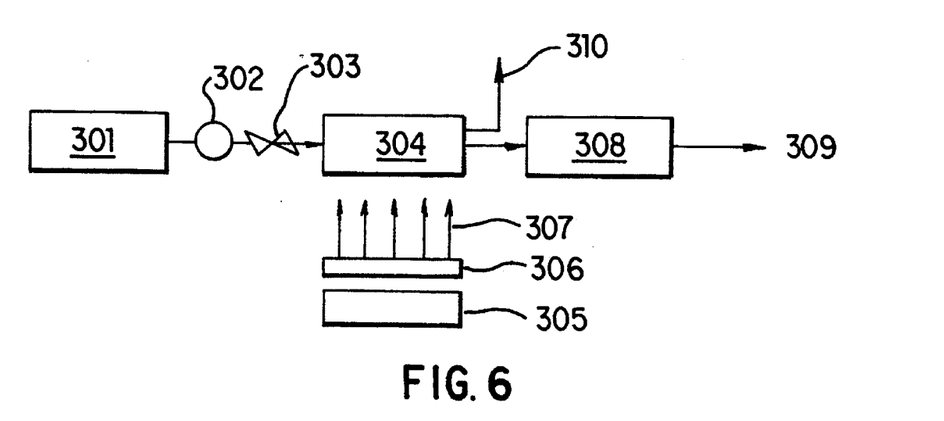
FIG. 6 shows a flow chart for photochemical conversion of dibenzylketone using the ICS system of the subject invention.

With reference to FIG. 6, dibenzylketone in benzene 301 (0.01 M) is metered via 302 and 303 into the photochemical reaction chamber 304 with at least one transparent wall, where it is irradiated with light 307 from a 450 watt xenon lamp 305 via filter 306. The CO produced 310, in the reaction 309 is vented and the bibenzyl product is purified, if desired, through a chromatographic separator 308 and withdrawn through line 309.

EXAMPLE 3

Electrochemical Reduction of Benzoquinone

Figure 7:
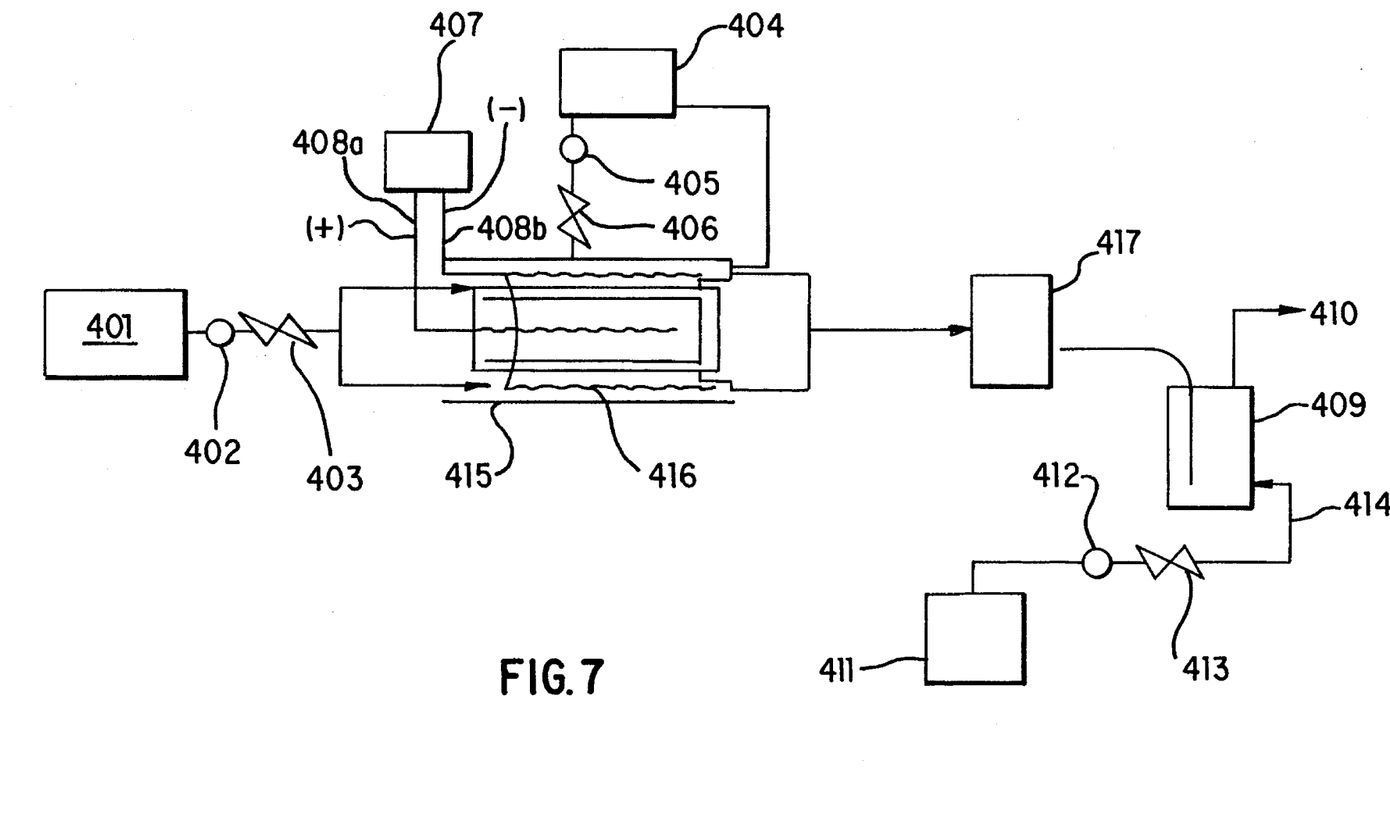
FIG. 7 is a flow chart illustrating electrochemical reduction of benzoquinone according to the present invention.

In FIG. 7, an acidic aqueous solution of benzoquinone (0.1 M) 401 is metered (402, 403) into the cathodic chamber 416 of the electrochemical reactor 415. This chamber, e.g. outside a Naflon hollow fiber tube containing the Pt anode and the analyte, contains a carbon or zinc cathode. Anode 408a and cathode 408b are connected to a power supply 407. The current density and flow rate are controlled to maximize current efficiency as determined by analysis of hydroquinone by the electrochemical detector 417. hydroquinone 410 is extracted in extractor 409 from the resulting product stream with ether 414 metered (412 and 413) from ether supply 411. Alternatively, flow in chamber 415 can be directed to the inner allode chamber with the appropriate controls.

EXAMPLE 4

Multiphase Membrane Reactor Conversion of Benzylpenicillin (BP) to 6-aminopenicillanic Acid (6-APA)

Figure 8:
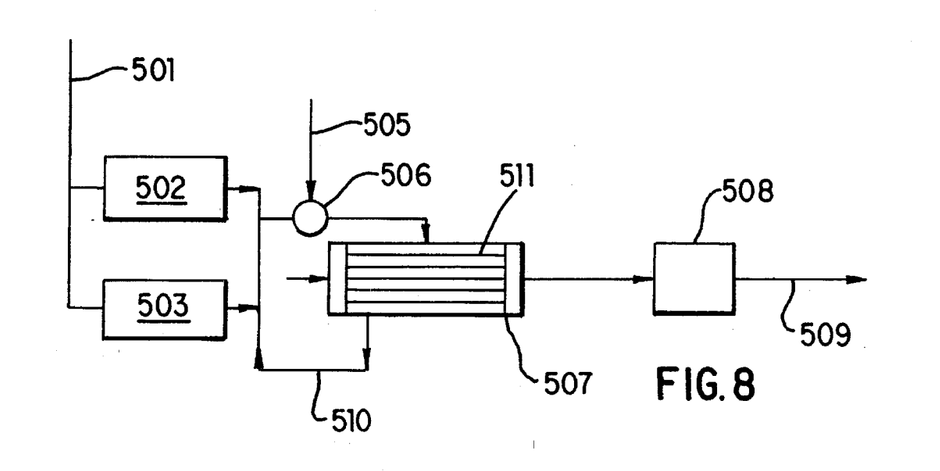
FIG. 8 is a flow chart for multiphase membrane reactor conversion of benzylpenicillin to 6 amino penicillanic acid (6-APA) using the ICS system.

In FIG. 8, the effluent 501 from a penicillin fermentation reactor containing BP is fed through a filter bank 502 and 503. An aqueous acid 505 is mixed with the filtered BP in mixer 506 and fed to membrane reactor 507. The membrane reactor 507 is preferably a hollow fiber tube 511 on which the enzyme penicillin acylase has been immobilized. The tube also selectively extracts 6-APA (see J. L. Lopez, S. L. Matson, T. J. Stanley, and J. A. Quinn, in "Extractive Bioconversions," Bioprocess Technologies Series, Vol 2, B. Masttgiasson and O. Holst. Eds., Marcel Dekker, N.Y., 1987). The BP is converted on the wall of the fiber and the product passes into the sweep stream inside the fiber where it can be purified by ion exchange 508. The BP stream 510 is recycled back through the reactor.

EXAMPLE 5

Catalytic Conversion (Reforming) of n-heptane to Toluene

Figure 9:
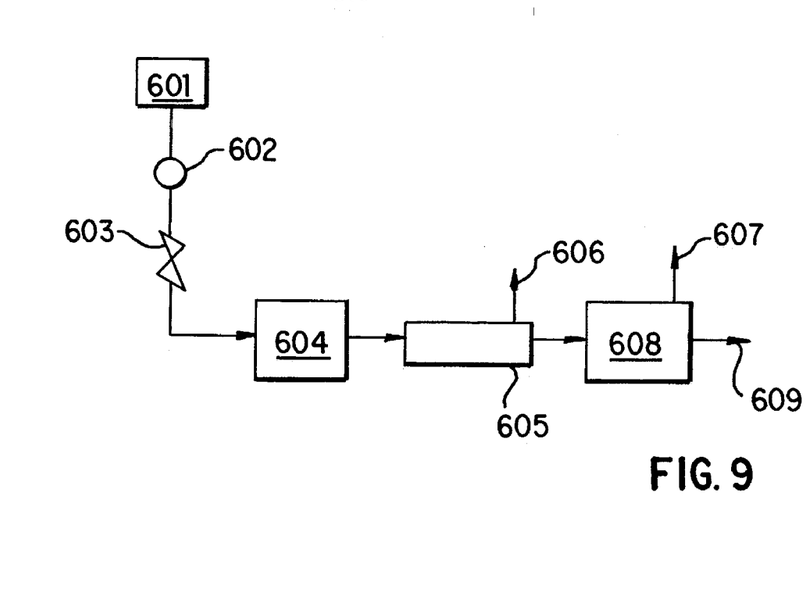
FIG. 9 is a flow chart for converting $n-C_7H_{16}$ to toluene using the subject invention.

In FIG. 9, liquid n-heptane 601 is metered via 602, 603 into the vaporizing chamber 604 held at 150° C. Toluene in the gas phase is conveyed to the catalytic reactor 605 containing a packed bed of Pt-$Al_2O_3$ catalyst held at 400° C. Hydrogen is removed through line 606. The heptane-toluene mixture from reactor 605 is fed to separator 608 with toluene being removed through line 609 and heptane through line 607.

Although the invention has been described in conjunction with the specific embodiments, it is evident that many alternatives and variations will be apparent to those skilled in the art in light of the foregoing description. Accordingly, the invention is intended to embrace all of the alternatives and variations that fall within the spirit and scope of the appended claims. Further, the subject matter of the above cited United States Patents are incorporated herein by reference.

We claim:

1. A modular chemical reaction system of independently detachable elements, said elements comprising:
    (a) at least one modular reactor having a reaction chamber volume from about 1nL to about 10 µL;
    (b) a separation chamber;
    (c) an analyzer chamber; and
    (d) an assembly board for laterally and independently mounting elements (a)–(c) thereon and providing flow communication therebetween.

2. A modular chemical reaction system as recited in claim 1, wherein said reaction chamber is selected from the group consisting of thermal, electrochemical, photochemical, and pressurized reaction chambers.

3. A modular chemical reaction system according to claim 1, wherein said separation chamber is selected from the group consisting of extraction, chromatographic, electrophoretic, membrane, and distillation separation chambers.

4. A modular chemical reaction system according to claim 1, wherein said analyzer is selected from the group consisting of electrochemical, spectroscopic, and fluorescence analyzers.

5. A modular chemical reaction kit comprising:
    (a) a support structure for laterally mounting and detachably retaining a plurality of physical and/or chemical process units in lateral position thereon;
    (b) a plurality of individual and independently detachable physical and/or chemical process units, at least one of said units being a reaction unit and another of said process units being structurally different and capable of permitting a different process to be performed, said plurality of individual and independently detachable physical and/or chemical process units being adapted for lateral mounting on said support structure;
    (c) a plurality of detachable and interchangeable flow channels;
    (d) at least one laterally disposed and detachable separation chamber;
    (e) at least one analyzer capable of monitoring and/or controlling a process variable; and
    (f) a computer interface for communicating a signal from (e) to a control system.

6. The kit according to claim 5, wherein there are at least three reaction units, two of which are identical.

7. The kit according to claim 5, wherein said flow channel and walls of said reaction unit are coated with $SiO_2$.

8. The kit according to claim 7, wherein said reaction unit has an I.D of about 1 µm to about 100 µm.

9. A method of making a modular reactor system having at least two laterally positionable treating chambers each having an ID less than 100 µm comprising,
    a) forming a first rectangular treatment chamber by,
        1) applying a photoresist layer onto an upper surface of a $SiO_2$ or Si substrate;
        2) developing a chamber design pattern on said layer;
        3) acid etching the exposed pattern to form a first treatment-reactor chamber having an ID less than 100 µm;
        4) covering an upper surface of the substrate with a cover to close the open upper surface of the first treatment-reactor chamber to form a reactor unit;
        5) repeating the applying, developing and etching steps above to form fluid conduits and fastening channels in said substrate; and
        6) repeating steps 1–5 above to form at least one second treatment chamber; said second treatment chamber capable of performing the same or different process than said first chamber; and
    b) laterally and independently mounting each of the at least two treatment chambers on an assembly board containing fluid conveying channels with fastening means to provide for flow to and from the treatment chambers.

10. A modular reactor comprising,
    1) a block substrate containing a chamber defining a volume of from about 1nL up to about 10 µL in volume having an inlet and outlet of lesser cross-sectional flow area than said chamber;
    2) flow channels formed within the block substrate for flow of reactants to and products from said reaction chamber;
    3) fastening means to permit said modular reactor to be connected to an assembly board.

11. A modular reactor according to claim 10, wherein said chamber volume is between about 1nL–1.01 µL in volume.

* * * * *